(12) United States Patent
Bernero

(10) Patent No.: US 8,252,058 B2
(45) Date of Patent: Aug. 28, 2012

(54) SPINAL IMPLANT WITH ELLIPTICAL ARTICULATORY INTERFACE

(75) Inventor: John P. Bernero, Round Rock, TX (US)

(73) Assignee: Amedica Corporation, Salt Lake City, UT (US)

( * ) Notice: Subject to any disclaimer, the term of this patent is extended or adjusted under 35 U.S.C. 154(b) by 224 days.

(21) Appl. No.: 11/307,681

(22) Filed: Feb. 16, 2006

(65) Prior Publication Data

US 2007/0191952 A1    Aug. 16, 2007

(51) Int. Cl.
*A61F 2/44* (2006.01)
(52) U.S. Cl. .................. 623/17.14; 623/17.15
(58) Field of Classification Search .......... 606/17.14, 606/17.15, 246, 249; 623/17.14, 17.15, 17.11, 623/17.12, 17.13, 17.16
See application file for complete search history.

(56) References Cited

U.S. PATENT DOCUMENTS

| | | |
|---|---|---|
| 3,867,728 A | 2/1975 | Stubstad et al. |
| 4,327,449 A | 5/1982 | Charnley |
| 4,695,282 A | 9/1987 | Forte et al. |
| 4,743,256 A | 5/1988 | Brantigan |
| 4,759,766 A | 7/1988 | Buettner-Janz et al. |
| 5,098,449 A | 3/1992 | Hwang et al. |
| 5,152,791 A | 10/1992 | Hakamatsuka et al. |
| 5,158,726 A | 10/1992 | Saita et al. |
| 5,192,327 A | 3/1993 | Brantigan |
| 5,314,477 A | 5/1994 | Marnay |
| 5,401,269 A | 3/1995 | Buttner-Janz et al. |
| 5,425,772 A | 6/1995 | Brantigan |
| 5,462,563 A | 10/1995 | Shearer et al. |
| 5,464,440 A | 11/1995 | Johansson |
| 5,549,704 A | 8/1996 | Sutter |
| 5,556,815 A | 9/1996 | Boberski |
| 5,609,635 A | 3/1997 | Michelson |
| 5,697,980 A | 12/1997 | Otani et al. |
| 5,702,449 A | 12/1997 | McKay |
| 5,702,453 A | 12/1997 | Rabbe et al. |

(Continued)

FOREIGN PATENT DOCUMENTS

WO    WO 96/40020    12/1996

(Continued)

OTHER PUBLICATIONS

International Search Report for PCT/US02/13654, Sep. 11, 2002, 2 pgs.

(Continued)

*Primary Examiner* — Eduardo C Robert
*Assistant Examiner* — Jan Christopher Merene
(74) *Attorney, Agent, or Firm* — Mintz Levin Cohn Ferris Glovsky and Popeo, P.C.

(57) ABSTRACT

A spinal implant prosthesis includes a pair of end plates for affixation to adjacent vertebral bone structures and respectively defining inter-engaged convex and concave articulatory surfaces of elliptical profile. These elliptical articulatory surfaces are elongated in an anterior-posterior direction, and are comparatively shorter in a medial-lateral direction. With this configuration, in response to angular displacement and/or axial rotation, the elliptical surfaces displace in a manner increasing the distance between the adjacent vertebral bone structures, thereby tensioning the prosthesis and producing counteracting forces which urge the components back toward a substantially centered or neutral position. In addition, in the preferred form, the anterior-posterior length of the concave articulatory surface in incrementally greater than the anterior-posterior length of the convex articulatory surface to accommodate a limited range of anterior-posterior translation.

12 Claims, 2 Drawing Sheets

U.S. PATENT DOCUMENTS

| | | | |
|---|---|---|---|
| 5,776,199 A | 7/1998 | Michelson | |
| 5,782,832 A | 7/1998 | Larson et al. | |
| 5,785,710 A | 7/1998 | Michelson | |
| 5,826,586 A | 10/1998 | Mishra et al. | |
| 5,861,041 A | 1/1999 | Tienboon | |
| 5,871,547 A | 2/1999 | Abouaf et al. | |
| 5,879,404 A | 3/1999 | Bateman et al. | |
| 5,879,407 A | 3/1999 | Waggener | |
| 5,888,222 A | 3/1999 | Coates et al. | |
| 5,888,223 A | 3/1999 | Bray | |
| 5,888,226 A * | 3/1999 | Rogozinski | 623/17.16 |
| 5,899,939 A | 5/1999 | Boyce et al. | |
| 5,904,720 A | 5/1999 | Farrar et al. | |
| 5,908,796 A | 6/1999 | Pujari et al. | |
| 6,013,591 A | 1/2000 | Ying et al. | |
| 6,033,438 A | 3/2000 | Bianchi et al. | |
| 6,037,519 A | 3/2000 | McKay | |
| 6,039,762 A | 3/2000 | McKay | |
| 6,039,763 A | 3/2000 | Shelokov | |
| 6,069,295 A | 5/2000 | Leitao | |
| 6,090,144 A | 7/2000 | Letot et al. | |
| 6,110,205 A | 8/2000 | Nies | |
| 6,113,637 A | 9/2000 | Gill et al. | |
| 6,133,180 A | 10/2000 | Miyake et al. | |
| 6,136,029 A | 10/2000 | Johnson et al. | |
| 6,136,369 A | 10/2000 | Leitao et al. | |
| 6,139,585 A | 10/2000 | Li | |
| 6,143,032 A | 11/2000 | Schafer et al. | |
| 6,149,686 A | 11/2000 | Kuslich et al. | |
| 6,149,688 A | 11/2000 | Brosnahan et al. | |
| 6,156,069 A | 12/2000 | Amstutz | |
| 6,179,874 B1 | 1/2001 | Cauthen | |
| 6,187,701 B1 | 2/2001 | Sekino et al. | |
| 6,210,612 B1 | 4/2001 | Pickrell et al. | |
| 6,235,665 B1 | 5/2001 | Pickrell et al. | |
| 6,245,108 B1 | 6/2001 | Biscup | |
| 6,261,322 B1 | 7/2001 | Despres, III et al. | |
| 6,261,586 B1 | 7/2001 | McKay | |
| 6,277,149 B1 | 8/2001 | Boyle et al. | |
| 6,281,264 B1 | 8/2001 | Salovey et al. | |
| 6,296,667 B1 | 10/2001 | Johnson et al. | |
| 6,302,913 B1 | 10/2001 | Ripamonti et al. | |
| 6,322,895 B1 | 11/2001 | Canham | |
| 6,344,061 B1 | 2/2002 | Leitao et al. | |
| 6,346,123 B1 | 2/2002 | McKay | |
| 6,368,350 B1 * | 4/2002 | Erickson et al. | 623/17.14 |
| 6,371,988 B1 | 4/2002 | Pafford et al. | |
| 6,376,573 B1 | 4/2002 | White et al. | |
| 6,398,811 B1 | 6/2002 | McKay | |
| 6,436,137 B2 | 8/2002 | Wang et al. | |
| 6,447,547 B1 | 9/2002 | Michelson | |
| 6,478,823 B1 | 11/2002 | Michelson | |
| 6,494,883 B1 | 12/2002 | Ferree | |
| 6,494,917 B1 | 12/2002 | McKellop et al. | |
| 6,511,510 B1 | 1/2003 | de Brujin et al. | |
| 6,517,580 B1 | 2/2003 | Ramadan et al. | |
| 6,527,810 B2 | 3/2003 | Johnson et al. | |
| 6,540,785 B1 * | 4/2003 | Gill et al. | 623/17.14 |
| 6,551,995 B1 | 4/2003 | Opperman et al. | |
| 6,554,867 B1 | 4/2003 | Joos | |
| 6,569,201 B2 | 5/2003 | Moumene et al. | |
| 6,587,788 B1 | 7/2003 | Green | |
| 6,610,097 B2 | 8/2003 | Serbousek et al. | |
| 6,641,617 B1 | 11/2003 | Merrill et al. | |
| 6,673,075 B2 | 1/2004 | Santilli | |
| 6,676,703 B2 | 1/2004 | Biscup | |
| 6,706,068 B2 | 3/2004 | Ferree | |
| 6,719,794 B2 | 4/2004 | Gerber et al. | |
| 6,723,097 B2 | 4/2004 | Fraser et al. | |
| 6,736,849 B2 | 5/2004 | Li et al. | |
| 6,740,118 B2 | 5/2004 | Eisermann et al. | |
| 6,758,849 B1 | 7/2004 | Michelson | |
| 6,790,233 B2 | 9/2004 | Brodke et al. | |
| 6,818,020 B2 | 11/2004 | Sun et al. | |
| 6,827,740 B1 | 12/2004 | Michelson | |
| 6,846,327 B2 | 1/2005 | Khandkar et al. | |
| 6,881,229 B2 | 4/2005 | Khandkar et al. | |
| 6,908,484 B2 | 6/2005 | Zubok et al. | |
| 6,972,037 B2 | 12/2005 | Zubok et al. | |
| 6,972,038 B2 | 12/2005 | Zubok et al. | |
| 6,989,030 B1 | 1/2006 | Ohgushi | |
| 6,994,728 B2 | 2/2006 | Zubok et al. | |
| 6,994,729 B2 | 2/2006 | Zubok et al. | |
| 6,997,954 B2 | 2/2006 | Zubok et al. | |
| 6,997,955 B2 | 2/2006 | Zubok et al. | |
| 7,051,417 B2 | 5/2006 | Michelson | |
| 7,066,961 B2 | 6/2006 | Michelson | |
| RE39,196 E | 7/2006 | Ying et al. | |
| 7,105,030 B2 | 9/2006 | Despres, III et al. | |
| 7,115,143 B1 | 10/2006 | Michelson | |
| 7,166,129 B2 | 1/2007 | Michelson | |
| 7,753,956 B2 * | 7/2010 | de Villiers et al. | 623/17.14 |
| 7,867,279 B2 * | 1/2011 | Hester et al. | 623/17.14 |
| 7,905,919 B2 * | 3/2011 | Kellar et al. | 623/16.11 |
| 8,142,505 B2 * | 3/2012 | Tauber | 623/17.14 |
| 2002/0062154 A1 | 5/2002 | Ayers | |
| 2002/0111680 A1 | 8/2002 | Michelson | |
| 2002/0143403 A1 | 10/2002 | Vaidyanathan et al. | |
| 2003/0040802 A1 * | 2/2003 | Errico et al. | 623/17.14 |
| 2003/0050709 A1 | 3/2003 | Noth et al. | |
| 2003/0135278 A1 * | 7/2003 | Eckman | 623/17.14 |
| 2003/0153984 A1 | 8/2003 | Khandkar et al. | |
| 2003/0204261 A1 * | 10/2003 | Eisermann et al. | 623/17.14 |
| 2003/0208273 A1 * | 11/2003 | Eisermann et al. | 623/17.14 |
| 2003/0233146 A1 * | 12/2003 | Grinberg et al. | 623/17.14 |
| 2004/0024462 A1 | 2/2004 | Ferree et al. | |
| 2004/0073312 A1 * | 4/2004 | Eisermann et al. | 623/17.14 |
| 2004/0133281 A1 | 7/2004 | Khandkar et al. | |
| 2004/0143332 A1 | 7/2004 | Krueger et al. | |
| 2004/0172135 A1 | 9/2004 | Mitchell | |
| 2004/0176772 A1 | 9/2004 | Zubok et al. | |
| 2004/0176845 A1 | 9/2004 | Zubok et al. | |
| 2004/0176850 A1 * | 9/2004 | Zubok et al. | 623/17.15 |
| 2004/0220670 A1 * | 11/2004 | Eisermann et al. | 623/17.14 |
| 2004/0220679 A1 | 11/2004 | Diaz et al. | |
| 2004/0225365 A1 * | 11/2004 | Eisermann et al. | 623/17.15 |
| 2004/0243241 A1 * | 12/2004 | Istephanous et al. | 623/17.14 |
| 2005/0043802 A1 * | 2/2005 | Eisermann et al. | 623/17.16 |
| 2005/0055098 A1 * | 3/2005 | Zdeblick et al. | 623/17.11 |
| 2005/0060034 A1 * | 3/2005 | Berry et al. | 623/17.11 |
| 2005/0060040 A1 | 3/2005 | Auxepaules et al. | |
| 2005/0079200 A1 | 4/2005 | Rathenow et al. | |
| 2005/0177238 A1 | 8/2005 | Khandkar et al. | |
| 2005/0177240 A1 | 8/2005 | Blain | |
| 2005/0216086 A1 * | 9/2005 | Marik et al. | 623/17.15 |
| 2005/0216092 A1 * | 9/2005 | Marik et al. | 623/23.39 |
| 2005/0251260 A1 * | 11/2005 | Gerber et al. | 623/17.13 |
| 2005/0251261 A1 * | 11/2005 | Peterman | 623/17.14 |
| 2005/0261772 A1 * | 11/2005 | Filippi et al. | 623/17.13 |
| 2005/0273176 A1 | 12/2005 | Ely et al. | |
| 2006/0041313 A1 * | 2/2006 | Allard et al. | 623/17.15 |
| 2006/0052875 A1 | 3/2006 | Bernero et al. | |
| 2006/0136062 A1 * | 6/2006 | DiNello et al. | 623/17.14 |
| 2006/0142862 A1 | 6/2006 | Diaz et al. | |
| 2006/0241772 A1 * | 10/2006 | Buettner-Janz et al. | 623/17.15 |
| 2007/0173942 A1 * | 7/2007 | Heinz et al. | 623/17.15 |
| 2007/0179615 A1 * | 8/2007 | Heinz et al. | 623/17.12 |
| 2008/0133013 A1 | 6/2008 | Duggal et al. | 623/17.16 |
| 2008/0183296 A1 * | 7/2008 | Ferree | 623/17.16 |
| 2009/0054986 A1 * | 2/2009 | Cordaro et al. | 623/17.15 |
| 2009/0062920 A1 * | 3/2009 | Tauber | 623/17.16 |
| 2009/0082868 A1 * | 3/2009 | Cordaro et al. | 623/17.16 |
| 2009/0210059 A1 * | 8/2009 | McCombe et al. | 623/17.14 |
| 2010/0191338 A1 * | 7/2010 | de Villiers et al. | 623/17.16 |
| 2011/0087331 A1 * | 4/2011 | Reichen et al. | 623/17.16 |

FOREIGN PATENT DOCUMENTS

| | | |
|---|---|---|
| WO | WO 99/20208 | 4/1999 |
| WO | WO 99/60956 | 12/1999 |
| WO | WO 00/49977 | 8/2000 |
| WO | WO 01/17464 | 3/2001 |
| WO | WO 2004/019828 | 3/2004 |
| WO | WO 2004/026186 | 4/2004 |
| WO | WO 2004/054479 | 7/2004 |
| WO | WO 2006119088 A2 * | 11/2006 |
| WO | WO 2006119092 * | 11/2006 |

OTHER PUBLICATIONS

International Search Report for PCT/US06/19254, Mar. 19, 2007, 1 pg.
Written Opinion for PCT/US06/19254, 3 pgs.
International Search Report for PCT/US06/31379, May 3, 2007, 1 pg.
International Search Report for PCT/US07/61972, Nov. 14, 2007, 1 pg.
International Search Report for PCT/US03/40086, Jul. 16, 2004, 1 pg.

* cited by examiner

SPINAL IMPLANT WITH ELLIPTICAL ARTICULATORY INTERFACE

BACKGROUND OF THE INVENTION

This invention relates generally to improvements in spinal implants of the type designed for human implantation between adjacent spinal vertebrae. More particularly, this invention relates to an improved spinal implant prosthesis including a pair of implant components defining inter-engaged articulatory surfaces having a generally elliptical profile shape and designed to accommodate limited and/or controlled articulatory movement.

Spinal implant devices are generally known in the art for surgical implantation between adjacent bony vertebral structures to correct or alleviate a number of clinical problems, such as degenerative disc disease, chronic back pain, spondylolisthesis, and others. In general terms, such spinal implants comprise a biocompatible construct formed from a relative high strength material such as titanium or cobalt chrome metal alloy, or a selected high strength ceramic, with a size and shape for intervertebral placement. In some designs, the implant has a porous region or regions adapted to receive autogenous or allogenous bone material, or otherwise defining a so-called porous bone ingrowth surface, for promoting bone ingrowth attachment of the implant device to the adjacent overlying and underlying vertebral structures. Such spinal implants are commonly used as fusion devices forming a substantially rigid interface between adjacent vertebral structures for alleviating specific patient symptoms. Alternative spinal implant designs comprise articulatory devices including upper and lower components adapted for respective fixation to overlying and underlying vertebral structures while defining an articulatory interface therebetween to maintain or restore normal or substantially normal patient movements.

A variety of articulatory spinal implant devices are known in the art. By way of example, U.S. Pat. No. 5,401,269 discloses one articulatory implant device having inter-engaged concave and convex surfaces defined by curved radial or part-circular arches, wherein the radius of the curved arches is greater in the anterior-posterior direction relative to a smaller arch radius in the medial-lateral direction. These different sizes of the inter-engaged arches in the anterior-posterior vs. medial-lateral directions beneficially accommodates a limited range of axial rotation between the articulatory surfaces, while producing counteracting forces that tend to return the engaged surfaces toward a normal neutral or non-rotated position. In addition, the engaged arched surfaces further accommodate a range of angular displacement. However, such angular displacement, e.g., in the anterior-posterior direction, or in the medial-lateral direction, is not accompanied by a counteracting or re-centering force tending to urge the engaged surfaces back toward a normal neutral position. Physical stops are provided to prevent excessive angular displacement between the implant components.

U.S. Pat. No. 6,113,637 discloses another articulatory spinal implant device having inter-engaged concave and convex surfaces of generally part-spherical or hemi-spherical shape, with the concave surface further including a centrally located cylindrical segment. This articulatory interface is designed to accommodate substantially unrestrained angular displacement as well as axial rotation between the engaged implant components, while additionally and beneficially permitting a range of fore-aft or anterior-posterior translation. Counteracting forces tending to resist over-displacement and tending to re-center the articulatory surfaces substantially in a neutral position are not present.

There exists a need for further improvements in and to articulatory spinal implant devices, particularly wherein a range of angular displacement and/or axial rotation between engaged articulatory surfaces is accompanied by counteracting forces urging return movement of the engaged surfaces substantially to an initial or neutral position, and further wherein the engaged articulatory surfaces accommodate a range of anterior-posterior displacement. The present invention fulfills these needs and provides further related advantages.

SUMMARY OF THE INVENTION

In accordance with the invention, a spinal implant prosthesis defines an inter-engaged pair of concave and convex articulatory surfaces of elliptical profile shape, wherein these articulatory surfaces are elongated in the anterior-posterior direction and are comparatively shorter in the medial-lateral direction. In the preferred form, the anterior-posterior length of the concave surface is greater than the anterior-posterior length of the convex surface by a selected increment. These articulatory surfaces accommodate a limited range of anterior-posterior translation therebetween, and further accommodate a range of relative angular displacement and/or axial rotation while applying a corresponding counteracting or re-centering force urging the implant components back toward a substantially centered or neutral position.

In the preferred form, the spinal implant comprises a pair of end plates, such as upper and lower end plates, formed from a suitable biocompatible construct and including affixation means for secure attachment respectively to adjacent overlying and underlying vertebral bone structures, as by means of fixation pins, bone cement, porous bone ingrowth surfaces, or a combination thereof. These end plates respectively define the inter-engaged convex and concave articulatory surfaces of elliptical profile. In one form, the upper end plate carries the convex articulatory surface for nested reception into and articulatory engagement with the concave surface carried by the lower end plate.

Each of the articulatory surfaces is defined by the substantially elliptical profile shape which is longer in the anterior-posterior direction and shorter in the medial-lateral direction. More particularly, in the anterior-posterior profile, the convex articulatory surface has an elongated shape defined by a major axis extending generally in the anterior-posterior direction and sized for nested reception into the concave articulatory surface which has an incrementally longer size and shape, i.e., an incrementally longer major axis also extending generally in the anterior-posterior direction. In the medial-lateral direction, the convex and concave articulatory surfaces define comparatively smaller elliptical profiles, i.e., comparatively smaller major axes which extend generally in the medial-lateral direction, and may be of substantially uniform size.

In use, the inter-engaged convex and concave articulatory surfaces of elliptical profile accommodate a range of relative angular displacement and relative axial rotation therebetween. However, as the two end plates are angularly displaced and/or axially rotated, the convex elliptical surface rides against the concave elliptical surface in a manner increasing the distance between the adjacent vertebral bone structures, thereby tensioning the prosthesis and producing a counteracting force or forces urging the components back toward a substantially centered or neutral position. In addition, the anterior-posterior size differential between the convex and concave articulatory surfaces accommodates a limited range of anterior-posterior translation therebetween.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
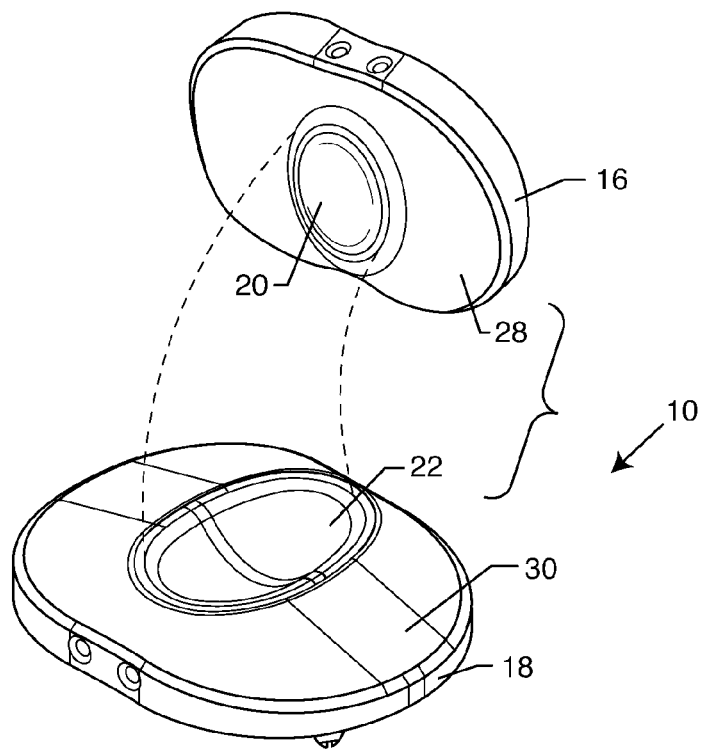
FIG. 1 is an exploded anterior or front perspective view of the spinal implant with elliptical articulatory interface embodying the novel features of the invention.

As shown in the exemplary drawings, a spinal implant referred to generally in FIGS. 1-5 by the reference numeral 10 is provided for surgical implantation into the intervertebral space between a pair of adjacent vertebral bone structures 12 and 14. The spinal implant 10 includes an upper component 16 and a lower component 18 adapted for respective affixation to the adjacent vertebral structures 12 and 14. The upper and lower components 16, 18 of the spinal implant 10 define inter-engaged convex and concave articulatory surfaces 20 and 22 of generally elliptical profile shape. These engaged articulatory surfaces 20, 22 are shaped to accommodate a limited range of angular displacement and/or axial rotation while producing a counteracting force or forces urging the components back toward a substantially centered or neutral position. In addition, the engaged articulatory surfaces 20, 22 accommodate a limited range of translation in an anterior-posterior direction.

The articulatory spinal implant device 10 of the present invention includes the upper and lower implant components 16 and 18 formed from a suitable biocompatible material with a size and shape for respective engagement with and secure affixation to the overlying and underlying adjacent bony vertebral structures 12 and 14. In this regard, the bone-facing surfaces of the two implant components 16, 18 may include projecting fins, teeth or pins 24 or the like designed to provide immediate stable anchored engagement with the adjoining vertebral structures. The two implant components 16, 18 may also include respective upper and lower surfaces 26 defined by or otherwise suitably coated with a porous bone ingrowth structure or substance to permit and accommodate relatively rapid bone ingrowth and osteo-integration for long term stable affixation to the adjoining vertebral structures.

The upper and lower implant components 16, 18 of the articulatory device 10 further define mutually facing bearing surfaces that are geometrically shaped for articulatory interengagement with each other in a manner intended to preserve and/or accommodate substantially normal anatomical intervertebral motion. The illustrative drawings show the upper implant component 16 to include an underside surface 28 in surrounding relation to the generally convex and centrally located articulatory surface or bearing member 20 protruding downwardly therefrom. This downwardly protruding convex articulatory surface 20 is received and movably supporting within the upwardly presented recessed or concave articulatory surface or bearing member 22 formed generally centrally within an upper surface 30 on the lower implant component 14.

In accordance with the invention, the inter-engaged convex and concave articulatory surfaces 20 and 22 are both formed with a generally elliptical profile shape. More particularly, both articulatory surfaces 20, 22 are shaped to define a generally elongated elliptical profile in the anterior-posterior direction, and a comparatively smaller elliptical profile in the medial-lateral direction. Accordingly, as viewed best in FIG. 1, the convex articulatory surface 20 is thus shaped to define a generally football-shaped structure extending downwardly from the surrounding underside surface 28 of the upper component 16, for movable seated reception into the upwardly presented concave articulatory surface 22 of generally football-shape formed generally centrally within the upper surface 30 of the lower component 18.

Figure 2:
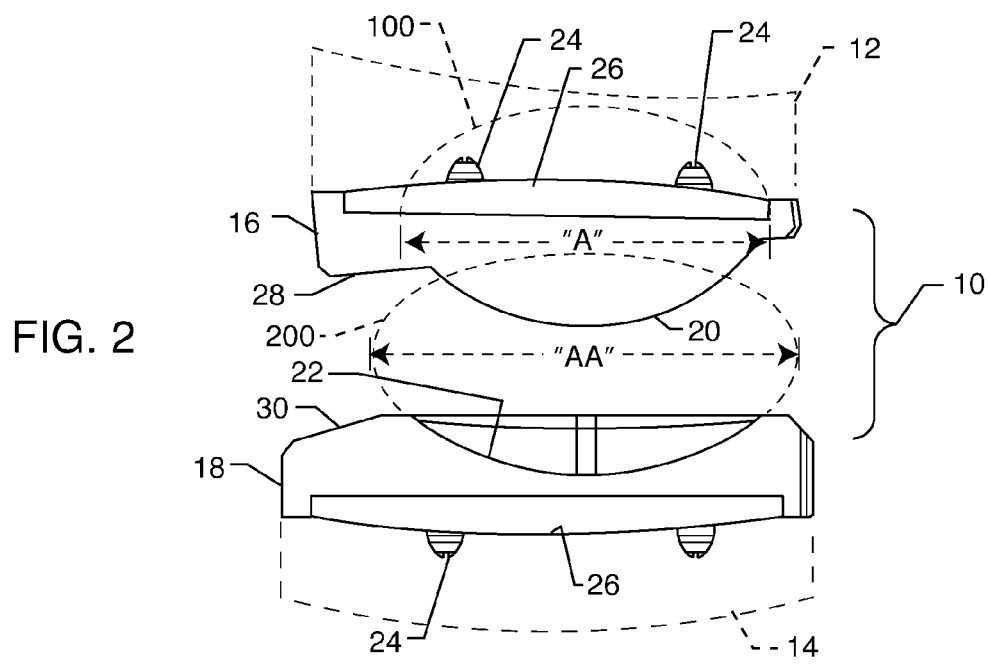
FIG. 2 is an exploded anterior-posterior vertical sectional view of the spinal implant of FIG. 1.
Figure 3:
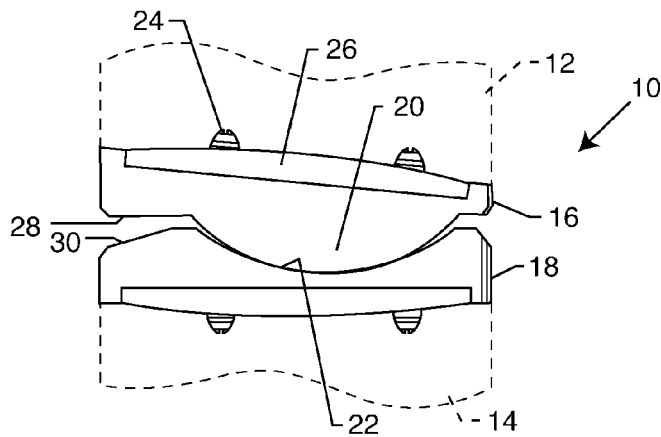
FIG. 3 is an anterior-posterior vertical sectional view similar to FIG. 2, but illustrating upper and lower components of the spinal implant in articulatory engagement.

The generally elliptical profile shape of the convex and concave articulatory surfaces 20, 22 in the anterior-posterior profile is shown best in FIGS. 2-3. As shown, the upper convex articulatory surface 20 is formed generally as a partial surface of an ellipse 100 having a major axis "A" extending generally in an anterior-posterior direction. This convex articulatory surface 20 seats within the upwardly presented concave articulatory surface 22 which is also formed generally as a partial surface of an ellipse 200 having a major axis "AA" having a dimension at least slightly larger than the dimension of the major axis "A" of the ellipse 100.

Figure 5:
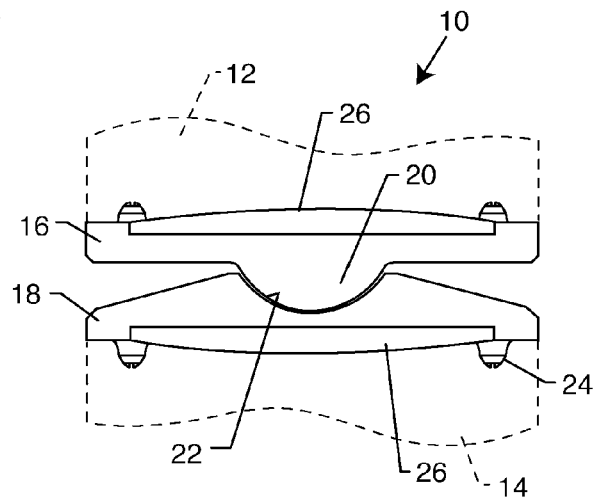
FIG. 5 is a medial-lateral vertical sectional view similar to FIG. 4, but showing the upper and lower implant components in articulatory engagement.
Figure 4:
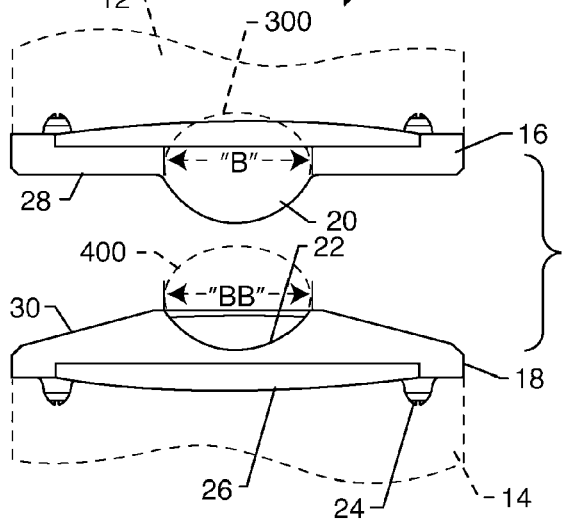
FIG. 4 is an exploded medial-lateral vertical sectional view of the spinal implant of FIG. 1.

FIGS. 4-5 show the elliptical profile shapes of the convex and concave articulatory surfaces 20, 22 in the medial-lateral profile. As shown, the upper convex articulatory surface 20 in the medial-lateral profile is formed generally as a partial surface of an ellipse 300 having a major axis "B" extending generally in the medial-lateral direction. The lower concave articulatory surface 22 is also formed generally as a partial surface of an ellipse 400 having a major axis "BB" with a dimension which may match or be substantially identical to the major axis "B" of the ellipse 300.

Accordingly, the upper convex articulatory surface 20 comprises a downwardly bulging structure having a shape corresponding generally to a segment of an ellipsoid defining the elongated major axis "A" extending generally in the anterior-posterior direction, and a shorter axis "B" extending generally in the medial-lateral direction. This convex ellipsoid structure 20 seats within the lower concave articulatory surface 22 comprising a recessed structure having a shape corresponding generally to a segment of an ellipsoid defining by the elongated major axis "AA" in the anterior-posterior direction, and the shorter axis "BB" extending generally in the medial-lateral direction. As noted, the major axis "AA" of the concave articulatory surface 22 is longer than the major axis "A" of the convex articulatory surface, whereas the shorter axes "BB" and "B" in the medial-lateral direction are substantially equal.

With this construction, when the convex and concave articulatory surfaces 20, 22 are engaged, controlled and relative movement is accommodated. Specifically, the size differential in the anterior-posterior direction permits a short increment of anterior-posterior translation between the upper and lower implant components 16, 18. In one preferred form, the size differential in the anterior-posterior direction is on the order of about ½ to about 3 millimeters, thereby permitting substantially unrestrained anterior-posterior translation within a range of about ½ to about 3 millimeters. However, as such translation approaches the limit, the anterior or posterior end of the convex elliptical surface 20 rides against the concave elliptical surface 22 to resist further displacement therebetween. That is, as the convex elliptical surface 20 rides up on the concave elliptical surface 22, the distance between the adjacent vertebral structures 12, 14 is increased, resulting in tensioning of the prosthetic joint to produce a counteracting force which resists further displacement and effectively urges the articulatory surfaces 20, 22 back toward a substantially centered or neutral position.

The same phenomenon occurs in response to relative angular displacement or relative axial rotation, or a combination thereof, between the two articulatory surfaces 20, 22. That is, the elliptical profile shape of the convex articulatory surface 20 rides against the elliptical profile shape of the concave articulatory surface 22, thereby urging the upper and lower components 16, 18 apart and thereby also increasing the spacing between the adjoining vertebral structures 12, 14. This results in tensioning of the prosthetic joint, to produce a counteracting force or forces that resists further displacement and effectively urges the articulatory surfaces 20, 22 back toward a substantially centered or neutral position.

FIGS. 3 and 5 show the convex articulatory surface 20 protruding downwardly from the upper component 16 a sufficient distance to maintain the surrounding underside surface 28 of the upper component 16 in spaced relation to the upper surface 30 of the lower component 18, when the convex surface 20 is seated in articulatory bearing engagement with the concave surface 22. In this regard, this inter-component spacing is desirably sufficient to maintain the component surfaces 28, 30 in spaced relation throughout a normal range of relative angular displacement on the order of about 5 to about 40 degrees, and preferably on the order of about 25 degrees.

A variety of further modifications and improvements in and to the improved articulatory spinal implant of the present invention will be apparent to those persons skilled in the art. By way of limited example, it will be understood that the upper convex and lower concave articulatory surfaces 20, 22 may be reversed, if desired. In addition, persons skilled in the art will appreciate that the anterior-posterior length of the concave surface 22 may be increased, relative to the convex surface, by incorporating a centrally located cylindrical segment within the otherwise elliptical profile shape of the concave surface 22. Accordingly, no limitation on the invention is intended by way of the foregoing description and accompanying drawings, except as set forth in the appended claims.

What is claimed is:

1. A spinal implant, comprising:
    a pair of implant components adapted for affixation respectively to adjacent vertebral structures and including inter-engageable articulatory bearing members;
    said bearing members including a convex articulatory surface and a concave articulatory surface both defined by a non-circular, generally elliptical profile shape in an anterior-posterior direction along a first plane, a non-circular, generally elliptical profile shape in a medial-lateral direction along a second plane, and a non-circular, generally elliptical profile shape when viewed on a third plane, the third plane being perpendicular to the first plane and second plane, wherein said convex articulatory surface and said concave articulatory surface are configured such that each of relative angular displacement, relative axial rotation, and simultaneous relative angular displacement and relative axial rotation of said articulatory surfaces results in a counteracting force which resists further relative angular displacement, relative axial rotation, or both, respectively, of the implant components and urges the articulatory surfaces back toward a neutral position.

2. The spinal implant of claim 1 wherein said concave articulatory surface is incrementally elongated relative to said convex articulatory surface in the anterior-posterior direction.

3. The spinal implant of claim 2 wherein said concave articulatory surface substantially matches said convex articulatory surface in the medial-lateral direction.

4. The spinal implant of claim 1 wherein said convex and concave articulatory surfaces are each formed as a segment of an ellipsoid.

5. The spinal implant of claim 1 wherein said pair of implant components each include means for affixation to adjacent vertebral structures.

6. A spinal implant, comprising:
    a pair of implant components adapted for affixation respectively to adjacent vertebral structures and including inter-engageable articulatory bearing members;
    said bearing members respectively including convex and concave articulatory surfaces each defined by a non-circular, generally elliptical profile shape in an anterior-posterior direction along a first plane, a non-circular, generally elliptical profile shape in a medial-lateral direction along a second plane, and a non-circular, generally elliptical profile shape when viewed on a third plane, the third plane being perpendicular to the first plane and second plane;
    said convex and concave surfaces being elongated in the anterior-posterior direction relative to the medial-lateral direction; and
    said concave articulatory surface being incrementally elongated relative to said convex articulatory surface in the anterior-posterior direction, and substantially matching each other in the medial-lateral direction, wherein said convex articulatory surface and said concave articulatory surface are configured such that each of relative angular displacement, relative axial rotation, and simultaneous relative angular displacement and relative axial rotation of said articulatory surfaces results in a counteracting force which resists further relative angular displacement, relative axial rotation, or both, respectively, of the implant components and urges the articulatory surfaces back toward a neutral position.

7. The spinal implant of claim 1 wherein each of said implant components includes a plurality of projections for anchored engagement with a respective one of said vertebral structures.

8. The spinal implant of claim 1 wherein each of said implant components includes a porous bone ingrowth structure for affixation to a respective one of said vertebral structures.

9. The spinal implant of claim 2 wherein said concave articulatory surface is about ½ to about 3 millimeters longer than said convex articulatory surface in the anterior-posterior direction.

10. The spinal implant of claim 6 wherein each of said implant components includes a plurality of projections for anchored engagement with a respective one of said vertebral structures.

11. The spinal implant of claim 6 wherein each of said implant components includes a porous bone ingrowth structure for affixation to a respective one of said vertebral structures.

12. The spinal implant of claim 6 wherein said concave articulatory surface is about ½ to about 3 millimeters longer than said convex articulatory surface in the anterior-posterior direction.

* * * * *